(12) United States Patent
Shin et al.

(10) Patent No.: US 8,442,267 B2
(45) Date of Patent: May 14, 2013

(54) APPARATUS AND METHOD FOR DETECTING UPPER BODY POSTURE AND HAND POSTURE

(75) Inventors: Ho Chul Shin, Daejeon (KR); Dan Hwan Hwang, Daejeon (KR); Jae Chan Jung, Daejeon (KR); Eui Gyoon Lim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 461 days.

(21) Appl. No.: 12/620,734

(22) Filed: Nov. 18, 2009

(65) Prior Publication Data

US 2010/0160835 A1   Jun. 24, 2010

(30) Foreign Application Priority Data

Dec. 24, 2008   (KR) ........................ 10-2008-0133228
Jul. 15, 2009   (KR) ........................ 10-2009-0064638

(51) Int. Cl.
*G06K 9/00*   (2006.01)

(52) U.S. Cl.
USPC ........................................................ 382/103

(58) Field of Classification Search .......... 382/100–107; 348/169–173
See application file for complete search history.

(56) References Cited

U.S. PATENT DOCUMENTS

2007/0230788 A1* 10/2007 Lei ................................ 382/186

FOREIGN PATENT DOCUMENTS

| KR | 10-2000-0006661 | 2/2000 |
|---|---|---|
| KR | 10-2002-0011851 | 2/2002 |
| KR | 10-2003-0002937 | 1/2003 |
| KR | 10-2004-0055310 | 6/2004 |
| KR | 10-2007-0055210 | 5/2007 |
| KR | 10-2007-0057613 | 6/2007 |

OTHER PUBLICATIONS

"Real-Time Human Body Posture Estimation Using a Stereo Vision Embedded System" by Young Keum Kim et al. on Computational Advances in Multi-Sensor Adaptive Processing. 2007. $2^{nd}$ IEEE International Workshop as of Dec. 12-14, 2007.

* cited by examiner

*Primary Examiner* — Atiba O Fitzpatrick
(74) *Attorney, Agent, or Firm* — Staas & Halsey LLP

(57) ABSTRACT

Provided are an apparatus and method which detect a user's upper body posture and the user's hand postures through at least two cameras to configure a user interface such as computers and home appliances. An apparatus for detecting upper body posture and hand posture includes a stereo vision calculation unit, a color pattern categorization unit, a plurality of position detection units, an upper body posture recognition unit, and a hand posture recognition unit. The stereo vision calculation unit calculates three-dimensional distance information from each image provided from at least two cameras. The color pattern categorization unit categorizes each color and pattern from the image to output color information and pattern information. The position detection units extract three-dimensional position information for each subject based on the three-dimensional distance information, the color information and the pattern information. The upper body posture recognition unit recognizes an upper body posture based on the three-dimensional position information. The hand posture recognition unit recognizes hand postures with hand position information of the three-dimensional position information.

18 Claims, 4 Drawing Sheets

APPARATUS AND METHOD FOR DETECTING UPPER BODY POSTURE AND HAND POSTURE

CROSS-REFERENCE TO RELATED APPLICATIONS

This application claims priority under 35 U.S.C. §119 to Korean Patent Application No. 10-2008-0133238, filed on Dec. 24, 2008, and Korean Patent Application No. 10-2009-0064638, filed on Jul. 15, 2009 in the Korean Intellectual Property Office, the disclosures of which are incorporated herein by reference in its entirety.

TECHNICAL FIELD

The following disclosure relates to an apparatus and method for detecting upper body posture and hand posture, and in particular, to an apparatus and method for detecting upper body posture and hand posture, which individually calculate and detect an upper body posture and a detailed hand posture in real time, and thus shorten calculation time taken in detection.

BACKGROUND

A background screen or a reference background screen is required for detecting the shape or motion of a person. That is, a related art lumps each part of body by using the difference between the reference background screen (or the background screen) and a current screen, and configures a human body model with each lump of body parts. For detecting a human body model or the shape or motion of a person, alternatively, the related art extracts feature points and calculates three-dimensional positions for each of the extracted feature points.

Accordingly, the related art requires the background screen or the reference background screen for detecting the shape or motion of a person. In the related art, it is substantially impossible to detect detailed motions such as hand postures, and much time is taken for calculation.

SUMMARY

In one general aspect, an apparatus for detecting upper body posture and hand posture includes: a stereo vision calculation unit calculating three-dimensional distance information from images which are provided from at least two cameras; a color pattern categorization unit categorizing each color and pattern from the images to output color information and pattern information; a plurality of position detection units extracting three-dimensional position information for each subject based on the three-dimensional distance information, the color information and the pattern information; an upper body posture recognition unit recognizing an upper body posture based on the three-dimensional position information for each subject; and a hand posture recognition unit recognizing hand postures with hand position information of the three-dimensional position information for each subject.

In another general aspect, an apparatus for detecting upper body posture and hand posture includes: a stereo vision calculation unit calculating three-dimensional distance information from images which are provided from at least two cameras; a color detection unit detecting a region having a skin color from the images; a pattern detection unit detecting a pattern for each body part from the images; a position detection unit categorizing each body part from the images and detecting a position of the each body part, by using the three-dimensional distance information, the region of the skin color and the pattern for each body part; an upper body posture recognition unit recognizing an upper body posture with the position of the each body part; and a hand posture recognition unit recognizing hand postures with hand position information of three-dimensional position information for each subject.

In another general aspect, a method for detecting upper body posture and hand posture includes: calculating three-dimensional distance information from images which are provided from at least two cameras; detecting a region having a skin color from the images; detecting a pattern for each body part from the images; detecting a position of the each body part by using the three-dimensional distance information, the region of the skin color and the pattern for each body part; recognizing an upper body posture with the position of the each body part; and recognizing hand postures based on hand position information of three-dimensional position information for each subject.

Other features and aspects will be apparent from the following detailed description, the drawings, and the claims.

DETAILED DESCRIPTION OF EMBODIMENTS

Figure 1:
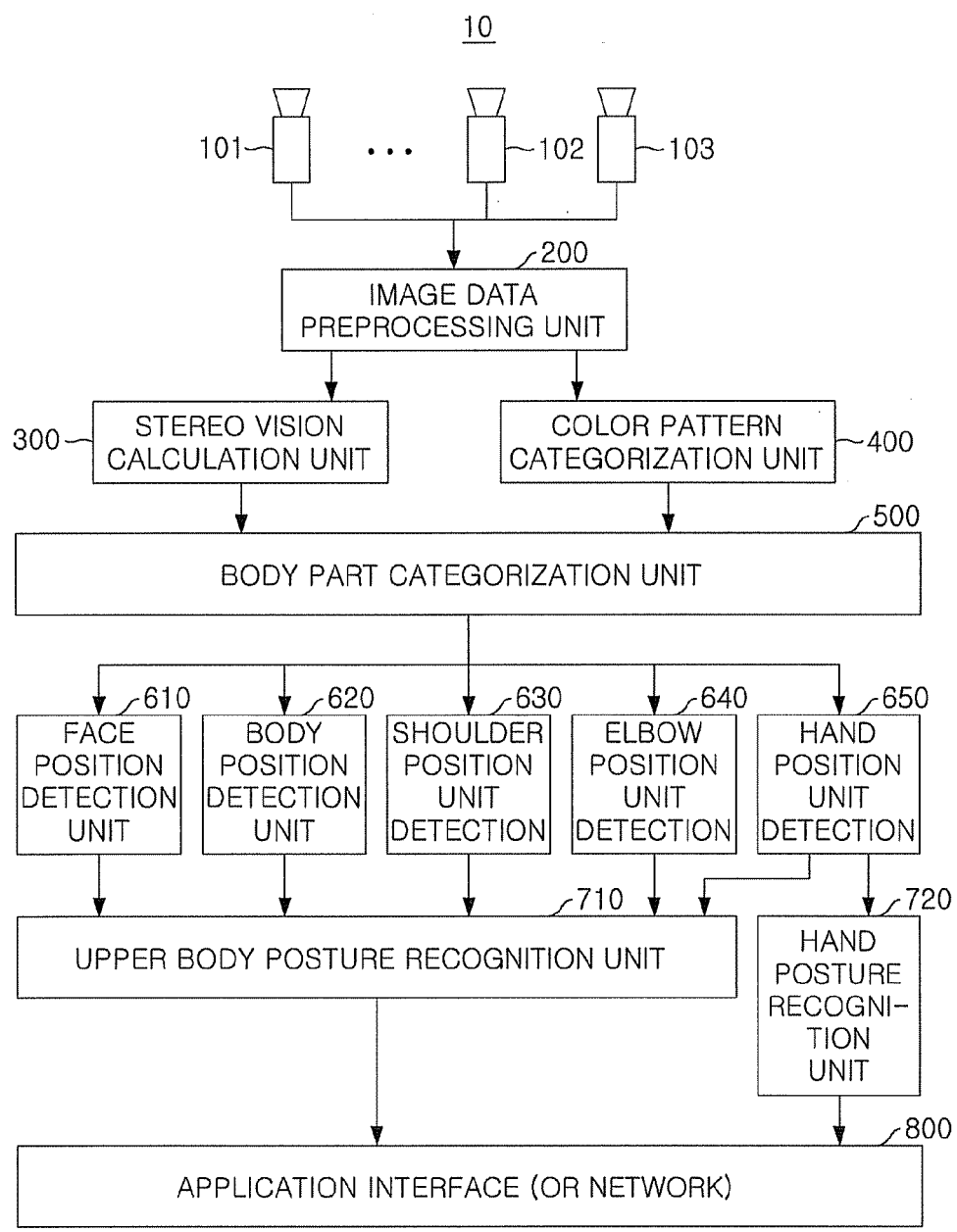
FIG. 1 is a block diagram illustrating an apparatus for detecting upper body posture and hand posture according to an embodiment of the present invention.

Hereinafter, exemplary embodiments will be described in detail with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience. The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 2:
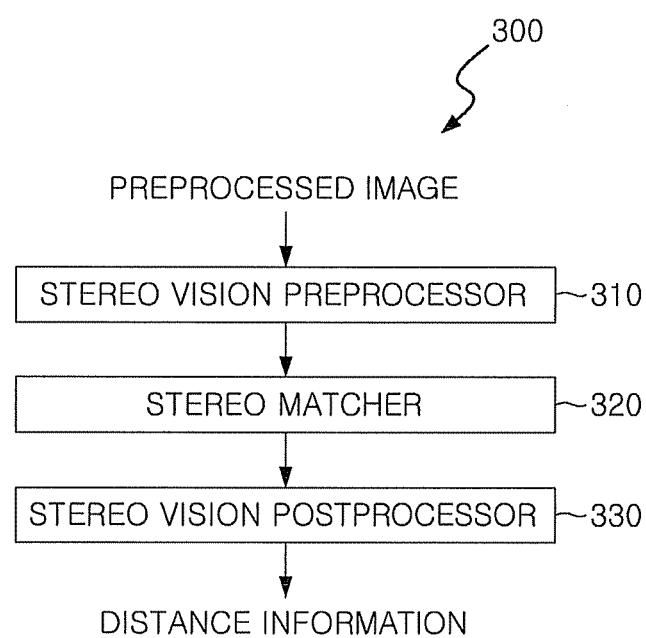
FIG. 2 is a block diagram illustrating a stereo vision calculation unit in FIG. 1.
Figure 3:
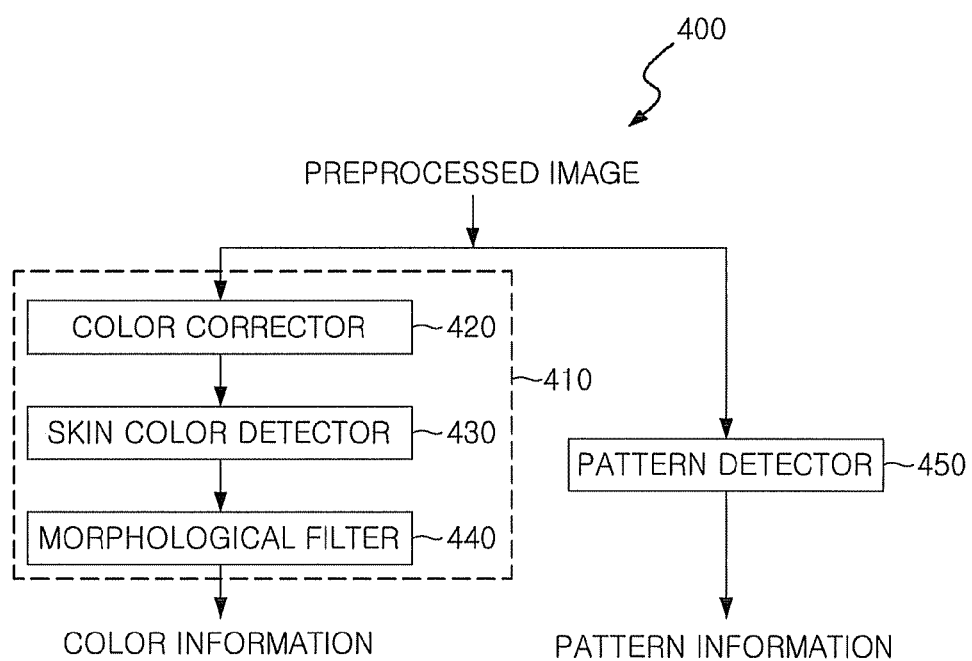
FIG. 3 is a block diagram illustrating a color pattern categorization unit in FIG. 1.

An apparatus and method for detecting upper body posture and hand posture according to an embodiment of the present invention will be described below with reference to FIGS. 1 to 3. FIG. 1 is a block diagram illustrating an apparatus for detecting upper body posture and hand posture according to an embodiment of the present invention. FIG. 2 is a block diagram illustrating a stereo vision calculation unit in FIG. 1. FIG. 3 is a block diagram illustrating a color pattern categorization unit in FIG. 1.

Referring to FIG. 1, an apparatus 10 for detecting upper body posture and hand posture according to an embodiment of the present invention includes at least two cameras 101 to 103, an image data preprocessing unit 200, a stereo vision calculation unit 300, a color pattern categorization unit 400, a body part categorization unit 500, a plurality of position detection units 610, 620, 630, 640 and 650, a upper body posture recognition unit 710, a hand posture recognition unit 720, and an application interface 300.

The cameras 101 to 103 photograph a person (hereinafter referred to as a user) to output images captured from a plurality of perspectives. The cameras 101 to 103, for example, may be disposed at home appliances such as computer monitors and televisions (TV) or walls and may be driven to photograph a user. As an example, the cameras 101 to 103 may move to recognize the user's motion or the user's voice and photograph the user.

The image data preprocessing unit 200 preprocesses image data that are provided from the cameras 101 to 103. For example, the image data preprocessing unit 200 may perform the improvement operations of image quality such as the removal of noise, the correction of color, the correction of brightness and the distortion correction of screen on the image data that are provided from the cameras 101 to 103. The preprocessed image is transferred to the stereo vision calculation unit 300 and the color pattern categorization unit 400.

First, the stereo vision calculation unit 300 calculates stereo images on images that are inputted from the cameras 101 to 103 and provides three-dimensional distance information from a subject to the respective cameras in a screen.

To provide a more detailed description with further reference to FIG. 2, the stereo vision calculation unit 300 includes a stereo vision preprocessor 310, a stereo matcher 320, and a stereo vision postprocessor 330.

The stereo vision preprocessor 310 controls the brightness of the cameras 101 to 103, removes noise or/and corrects distortion for stereo matching. Alternatively, the stereo vision preprocessor 310 may perform calibration, scale filtering, rectification and brightness control.

The stereo matcher 330 finds stereo matching portions from the preprocessed imaged of the cameras 101 to 103 to extract distance information. At this point, the distance information outputted from the stereo matcher 320, for example, may be an image that is represented as brightness according to distance (herein an image in which a near subject is represented as a bright color and a far subject is represented as a dark color) or an image in which subjects are represented as different colors according to distance). Herein, a far background may be deleted.

The vision postprocessor 320 post-processes and outputs distance information that is outputted from the stereo matcher 320. For example, the stereo vision postprocessor may remove noise from the distance information that is outputted from the stereo matcher 320, or segment and label different subjects from the distance information.

Next, the color pattern categorization unit 400 in FIG. 1 categorizes and analyzes colors and patterns in a screen to output color information and pattern information for recognizing a user's body parts, for example, a face, a body, shoulders, elbows and hands.

To provide a more detailed description with reference to FIG. 3, the color pattern categorization unit 400 includes a color detector 410 and a pattern detector 450.

The color detector 410 includes a color corrector 420, a skin color detector 430, and a morphological filter 440.

The color corrector 420 corrects colors from an image that is preprocessed by the image data preprocessing unit 200. For example, when an entire image is red, the color corrector 420 decreases a red component. Alternatively, the color corrector 420 may control the rate of the red (R), green (G) and blue (B) components of an image.

The skin color detector 430 may detect a skin color from the corrected image. That is, the skin color detector 430 may a region having a skin color from the corrected image.

The morphological filter 440 determines the morphology of a region having a skin color by filtering to output color information that corresponds to the determined morphology. For example, the morphological filter 440 may determine the edge of a region having a skin color, which is outputted from the skin color detector 430, to determine the morphology of the region having the skin color by morphological filtering.

Subsequently, the pattern detector 450 detects pattern information from an image that is preprocessed by the image data preprocessor 200. The pattern detector 450 may detect a pattern for each body part from the preprocessed image. As an example, the pattern detector 450 may detect a region having the patterns of a face, a body, shoulders, elbows and hands from the preprocessed image. The pattern detector 450, for example, may compare an image with the prestored pattern samples of a face, a body, shoulders, elbows and hands to detect a region having the patterns of the face, the body, the shoulders, the elbows and the hands from the image.

The stereo vision calculation unit 300 and the color pattern categorization unit 400 processes in individual and in parallel an image that is preprocessed by the image data preprocessing unit 200, shortening calculation time. In the color pattern categorization unit 400, moreover, the color detector 410 and the pattern detector 450 operate in individual and in parallel, thereby shortening calculation time.

The body part categorization unit 500 in FIG. 1 may categorize each body part from an image based on three-dimensional distance information that is outputted from the stereo vision calculation unit 300 and color information and pattern information that are outputted from the color pattern categorization unit 400. That is, the body part categorization unit 500 categorizes the face, body, shoulders, elbows and hands of a user from the image.

The position detection units 610, 620, 630, 640 and 650 detect the positions of body parts, respectively. For example, the face position detection unit 610 detects the three-dimensional position of a user's face, and the body position detection unit 620 detects the three-dimensional position of the user's body. The shoulder position detection unit 630 detects the three-dimensional positions of the user's shoulders, and the elbow position detection unit 640 detects the three-dimensional positions of the user's elbows. The hand position detection unit 650 detects the three-dimensional positions of the user's hands.

The position detection units 610, 620, 630, 640 and 650 detect the respective positions of body parts in individual and in parallel, shortening calculation time. The position detection units 610, 620, 630, 640 and 650 use three-dimensional position information that is generated based on the three-dimensional distance information, color information and pattern information of each body part, thereby detecting each body part in detail.

The upper body posture recognition unit 710 recognizes the user's upper body posture with three-dimensional position information for each body part. For example, the upper body posture recognition unit 710 reconfigures the user's upper body posture based on the three-dimensional information of a face, a body, shoulders, elbows and hands, thereby recognizing the user's upper body posture.

The hand posture recognition unit 720 may recognize the user's hand postures based on the three-dimensional position information of the hands.

The upper body posture information and the hand posture information are transferred to external devices (or network) through the application interface 800 and are thereby used.

As described above, the apparatus 10 individually generates three-dimensional distance information, color information and pattern information, and separately detects the postures of a face, a body, shoulders, elbows and hands with these information, shortening calculation time. Moreover, the apparatus 10 detects the detailed postures of the hands in real time based on the three-dimensional distance information, the color information and the pattern information. Furthermore, the apparatus 10 is connected to an external device to control in detail the external device according to a user's upper body posture and the user's hand postures. For example, the apparatus 10 may performs different controls based on the upper body posture and the hand postures. That is, the user may issue different commands even in the same posture because hand postures are recognized, and thus various applications may be configured.

Figure 4:
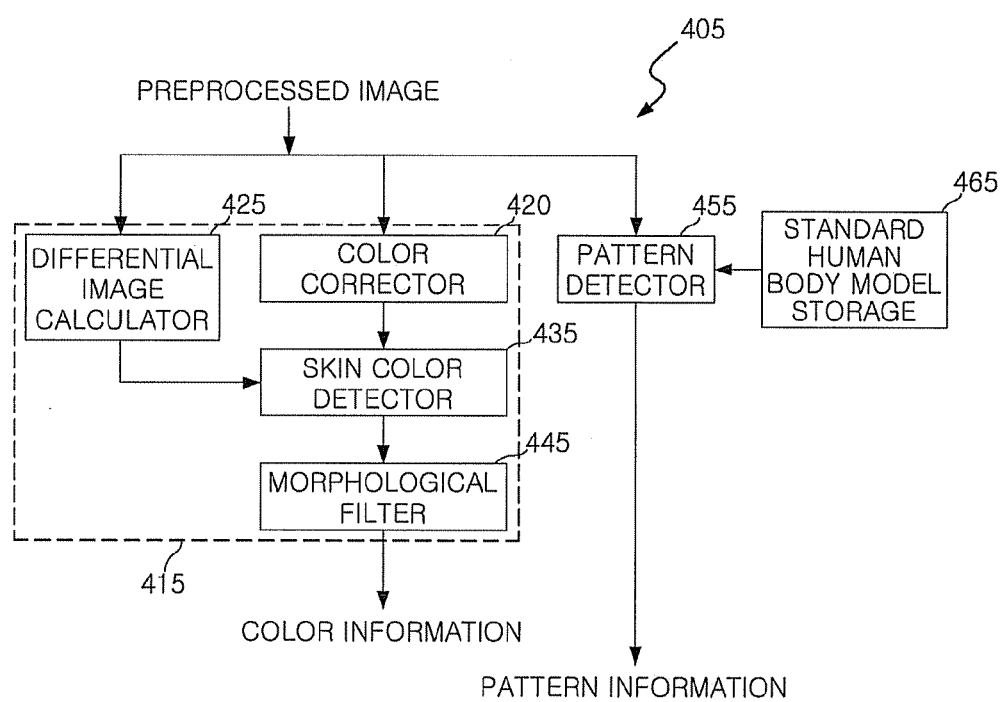
FIG. 4 is a block diagram illustrating the color pattern categorization unit of an apparatus for detecting upper body posture and hand posture according to another embodiment of the present invention.

An apparatus and method for detecting upper body posture and hand posture according to another embodiment of the present invention will be described below with reference to FIG. 4. FIG. 4 is a block diagram illustrating the color pattern categorization unit of an apparatus for detecting upper body posture and hand posture according to another embodiment of the present invention.

Referring to FIG. 4, a color pattern categorization unit 405 includes a color detector 415, a pattern detector 455, and a standard human body model storage 465.

The color detector 415 includes a color corrector 420, a differential image calculator 425, a skin color detector 435, and a morphological filter 445.

The color corrector 420 corrects colors from a preprocessed image. When an entire image is red, the color corrector 420 may decrease a red component. Alternatively, the color corrector 420 may control the rate of the red (R), green (G) and blue (B) components of an image.

The differential image calculator 425 calculates a differential image being the difference between a current image and a previous image. Herein, the differential image is used to detect a skin color from a corrected image in the skin color detector 435.

Specifically, the differential image calculator 425 subtracts a previous image from a current image to calculate a differential image and a motion vector. The differential image is an image of the previous image subtracted from the current image and is an image for a changed region (or a moved region). The motion vector is information representing the changed region (or the moved region), for example, represents the direction and magnitude of change or motion. In the current image and the previous image, because a moved subject may be a person, the differential image may be the image of a person and includes the skin color region of a person. That is, the motion vector, which is information representing the differential image, has information on a person's skin color. Accordingly, the skin color detector 435 analyzes the color of the changed region (or the moved region) to recognize a skin color by use of the differential image or the motion vector, and detects a skin color from a corrected image by use of the recognized skin color. In this case, the differential image calculator 425 does not detect a skin color from an image by using a skin color for detection that has certain brightness and chroma, and detects a skin color from an image by using the skin color of a actually-photographed person, obtaining more accurate and reliable result.

The morphological filter 445 determines the morphology of a region having a skin color by filtering to output color information that corresponds to the determined morphology. For example, the morphological filter 445 may determine the edge of a region having a skin color, which is outputted from the skin color detector 435, to determine the morphology of a region having a skin color by morphological filtering.

Subsequently, the pattern detector 455 detects pattern information, for example, information on the position and morphology of each body part, from a preprocessed image by use of a standard human body model that is stored in the standard human body model storage 465. The body rates of people, the morphology of each body part and the position of each body part represent constant tendencies based on sex and age, and standardizing these is a standard human body model. The standard human body model may be a sample on a body rate and the morphology and position of each body part based on sex and age. The pattern detector 455 detects information of the position and morphology of each body part from an image based on the standard human body model, detecting more accurate information.

A number of exemplary embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for detecting upper body posture and hand posture, comprising:
   a stereo vision calculation unit calculating three-dimensional distance information from images which are provided from at least two cameras;
   a color pattern categorization unit, in parallel to the calculating, categorizing each color and pattern from the images to output color information and pattern information where the categorizing of each color and pattern is in parallel;
   a plurality of position detection units, in parallel, extracting three-dimensional position information for each subject based on the three-dimensional distance information, the color information and the pattern information;
   an upper body posture recognition unit recognizing an upper body posture based on the three-dimensional position information for each subject; and
   a hand posture recognition unit recognizing hand postures with hand position information of the three-dimensional position information for each subject.

2. The apparatus of claim 1, further comprising an image data preprocessing unit performing at least one of noise removal, color correction, brightness correction and distortion correction of a screen on the image which is inputted from each of the at least two cameras.

3. The apparatus of claim 1, wherein:
   the subject comprises a face, a body, shoulders, elbows and hands, and
   the position detection units comprise a face position detection unit, a body position detection unit, a shoulder position detection unit, an elbow position detection unit, and a hand position detection unit.

4. The apparatus of claim 3, wherein the upper body posture recognition unit reconfigures an upper body of a person based on information of the face, information of the body, information of the shoulders, information of the elbows and information of the hands to recognize the upper body posture.

5. The apparatus of claim 1, wherein the color pattern categorization unit comprises:
   a color detector detecting the color information from the images; and
   a pattern detector detecting the pattern information from the images.

6. The apparatus of claim 5, wherein the color detector comprises:
   a color corrector correcting each color of the images;
   a differential image calculator calculating a differential image which is a difference between the image and a previous image;
   a skin color detector detecting a region of a skin color with the image having the corrected color and the differential image; and
   a morphological filter determining a morphology of the region of the skin color by filtering to output the color information which corresponds to the determined morphology.

7. The apparatus of claim 5, wherein:
   the color pattern categorization unit further comprises a standard human body model storage storing a standard human body model, and
   the pattern detector detects pattern for each body part from the images by using the standard human body model to output the pattern information which corresponds to the detected pattern for each body part.

8. The apparatus of claim 1, wherein the stereo vision calculation unit comprises:
   a stereo vision preprocessor preprocessing the images which are provided from the at least two cameras;
   a stereo matcher extracting distance information from the preprocessed images; and
   a stereo vision postprocessor post-processing the distance information.

9. An apparatus for detecting upper body posture and hand posture, comprising:
   a stereo vision calculation unit calculating three-dimensional distance information from images which are provided from at least two cameras;
   a color detection unit, in parallel with the calculating, detecting a region having a skin color from the images;
   a pattern detection unit detecting, in parallel with the calculating and in parallel with the detecting the region, a pattern for each body part from the images;
   a position detection unit categorizing each body part from the images and detecting, in parallel, a position of the each body part, by using the three-dimensional distance information, the region of the skin color and the pattern for each body part;
   an upper body posture recognition unit recognizing an upper body posture with the position of the each body part; and
   a hand posture recognition unit recognizing hand postures with hand position information of three-dimensional position information for each subject.

10. The apparatus of claim 9, wherein the color detection unit comprises:
    a color corrector correcting each color of the images;
    a skin color detector detecting a region of a skin color from the images having the corrected color; and
    a morphological filter determining an edge of the skin color by morphological filtering.

11. The apparatus of claim 9, wherein the pattern detection unit compares the image with a prestored pattern sample for each body part to detect the pattern for each body part.

12. The apparatus of claim 9, wherein:
    the body parts comprise a face, a body, shoulders, elbows and hands, and
    the upper body posture recognition unit reconfigures an upper body of a person based on information of the face, information of the body, information of the shoulders, information of the elbows and information of the hands to recognize the upper body posture.

13. The apparatus of claim 9, further comprising an interface transferring information on the upper body posture and the hand postures to an outside.

14. A method for detecting upper body posture and hand posture, comprising:
    calculating three-dimensional distance information from images which are provided from at least two cameras;
    detecting, in parallel with the calculating, a region having a skin color from the images;
    detecting, in parallel with the calculating and in parallel with the detecting the region, a pattern for each body part from the images;
    detecting, in parallel, a position of the each body part by using the three-dimensional distance information, the region of the skin color and the pattern for each body part;
    recognizing an upper body posture with the position of the each body part; and
    recognizing hand postures based on hand position information of three-dimensional position information for each subject.

15. The method of claim 14, further comprising performing at least one of noise removal, color correction, brightness correction and distortion correction of a screen on an image which is inputted from each of the at least two cameras.

16. The method of claim 14, wherein the detecting of a region having a skin color comprises:
    correcting each color of the images;
    calculating a differential image which is a difference between the image and a previous image;
    detecting a region of a skin color by using the image having the corrected color and the differential image; and
    determining an edge of the region of the skin color by morphological filtering.

17. The method of claim 14, wherein the detecting of a position of the each body part comprises categorizing the each body part from the image by using the three-dimensional distance information, the region of the skin color and the pattern for each body part.

18. The method of claim 14, wherein:
    the body parts comprise a face, a body, shoulders, elbows and hands, and
    the recognizing of an upper body posture reconfigures an upper body of a person based on information of the face, information of the body, information of the shoulders, information of the elbows and information of the hands to recognize the upper body posture.

* * * * *